US010561329B2

(12) United States Patent
Wang et al.

(10) Patent No.: US 10,561,329 B2
(45) Date of Patent: Feb. 18, 2020

(54) METHOD AND SYSTEM FOR ECG BASED CARDIAC ISCHEMIA DETECTION

(71) Applicant: KONINKLIJKE PHILIPS N.V., Eindhoven (NL)

(72) Inventors: Jyh-Yun John Wang, Newton, MA (US); Bohumil Horacek, Halifax (CA); James Warren, Halifax (CA)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 144 days.

(21) Appl. No.: 15/562,000

(22) PCT Filed: Mar. 29, 2016

(86) PCT No.: PCT/IB2016/051761
§ 371 (c)(1),
(2) Date: Sep. 27, 2017

(87) PCT Pub. No.: WO2016/166627
PCT Pub. Date: Oct. 20, 2016

(65) Prior Publication Data
US 2018/0055401 A1    Mar. 1, 2018

Related U.S. Application Data

(60) Provisional application No. 62/147,122, filed on Apr. 14, 2015, provisional application No. 62/187,295, filed on Jul. 1, 2015.

(51) Int. Cl.
*A61B 5/0452* (2006.01)
*A61B 5/04* (2006.01)
(Continued)

(52) U.S. Cl.
CPC .......... *A61B 5/04525* (2013.01); *A61B 5/044* (2013.01); *A61B 5/04012* (2013.01);
(Continued)

(58) Field of Classification Search
CPC .......... A61B 5/0425; A61B 5/04012
(Continued)

(56) References Cited

U.S. PATENT DOCUMENTS

2002/0087088 A1    7/2002    Brodnick
2006/0264770 A1*  11/2006    Wellens ............. A61B 5/04011
                                                            600/509
(Continued)

OTHER PUBLICATIONS

Horáček et al., "Optimal electrocardiographic leads for detecting acute myocardial ischemia", J Electrocardiol 2001;34 (Suppl):97-111).
(Continued)

*Primary Examiner* — Nadia A Mahmood

(57) ABSTRACT

An acute ischemia detection device comprises a 12-lead electrocardiograph (ECG) device (12), an electronic data processing device (12), and a display component (22). The electronic data processing device applies 12-lead ECG to vessel-specific lead (VSL) transforms (50) to 12-lead ECG data acquired by the 12-lead ECG device to generate VSL lead data (e.g., LAD, LCX, and RCA vessel-specific lead data), determines ST values for the VSL lead data, and decides whether the 12-lead ECG data acquired by the 12-lead ECG device indicates acute ischemia by comparing the ST values for the VSL lead data with VSL lead ST thresholds (60). The display component may display an acute ischemia alarm or warning if the decision is the 12-lead ECG data acquired by the 12-lead ECG device indicates acute ischemia, and/or may display the generated VSL lead ECG traces.

8 Claims, 6 Drawing Sheets

(51) Int. Cl.
*A61B 5/0428* (2006.01)
*A61B 5/044* (2006.01)
*A61B 5/0472* (2006.01)
*A61B 5/00* (2006.01)

(52) U.S. Cl.
CPC .......... *A61B 5/0452* (2013.01); *A61B 5/0472* (2013.01); *A61B 5/04286* (2013.01); *A61B 5/746* (2013.01)

(58) Field of Classification Search
USPC ........................................................ 600/523
See application file for complete search history.

(56) References Cited

U.S. PATENT DOCUMENTS

| | | |
|---|---|---|
| 2009/0048528 A1 | 2/2009 | Hopenfeld |
| 2012/0010515 A1 | 1/2012 | Zhou |
| 2012/0323133 A1 | 12/2012 | Lindauer |
| 2013/0237870 A1 | 9/2013 | Gregg |

OTHER PUBLICATIONS

Horáček et al., "Detection of myocardial ischemia by vessel-specific leads derived from the 12-lead electrocardiogram and its subsets", J Electrocardiol 2008;41:508-517).

Horáček et al., "On designing and testing transformations for derivation of standard 12-lead/18-lead electrocardiograms and vectorcardiograms from reduced sets of predictor leads", J Electrocardiol 2008;41:220-229).

Martin, et al., "ST-Segment Deviation Analysis of the Admission 12-Lead Electrocardiogram as an Aid to Early Diagnosis of Acute Myocardial Infarction With a Cardiac Magnetic Resonance Imaging Gold Standard" Journal of the American College of Cardiology, vol. 50, No. 11, 2007.

Rautaharju, et al., "AHA/ACCF/HRS Recommendations for the Standardization and Interpretation of the Electrocardiogram Part IV: The ST Segment, T and U Waves, and the QT Interval a Scientific Statement From the American Heart Association Electrocardiography and Arrhythmias Committee, Council on Clinical Cardiology; the American College of Cardiology", Feb. 19, 2009; American Heart Association.

Antman, et al., "A Report of the American College of Cardiology/American Heart Association Task Force on Practice Guidelines" JACC vol. 51, No. 2, 2008; American Heart Association.

Kligfield, et al., Recommendations for the Standardization and Interpretation of the Electrocardiogram Part I: The Electrocardiogram and Its Technology a Scientific Statement From the American Heart Association Electrocardiography and Arrhythmias Committee, Council on Clinical Cardiology; the American College of Cardiology Foundation; and the Heart Rhythm Society, Feb. 23, 2007; American Heart Association.

Wagner, et al., "AHA/ACCF/HRS Recommendations for the Standardization and Interpretation of the Electrocardiogram Part VI: Acute Ischemia/Infarction a Scientific Statement From the American Heart Association Electrocardiography and Arrhythmias Committee, Council on Clinical Cardiology; the American College of Cardiology Foundation; and the Heart Rhythm Society" Feb. 19, 2009, American Heart Association.

Thygesen, et al., "Universal Definition of Myocardial Infarction", Journal of the American College of Cardiology, vol. 50, No. 22, 2007.

Kornreich, et al., Body Surface Potential Mapping of ST Segment Changes in Acute Myocardial Infarction Implications or ECG Enrollment Criteria for Thrombolytic Therapy; Circulation vol. 87, No. 3 Mar. 1993.

Part 5: Acute Coronary Syndromes, Circulation 2005;112;III-55-III-72, American Heart Association.

Ornato, et al., "Body surface mapping vs 12-lead electrocardiography to detect ST-elevation myocardial infarction", American Journal of Emergency Medicine, vol. 27 Issue: 7 pp. 779-784.

* cited by examiner

METHOD AND SYSTEM FOR ECG BASED CARDIAC ISCHEMIA DETECTION

CROSS REFERENCE TO RELATED APPLICATIONS

This application is the U.S. National Phase application under 35 U.S.C. § 371 of International Application No. PCT/IB2016/051761 filed Mar. 29, 2016, published as WO 2016/166627 on Oct. 20, 2016, which claims the benefit of U.S. Provisional Patent Application No. 62/147,122 filed Apr. 14, 2015 and U.S. Provisional Patent Application No. 62/187,295 filed Jul. 1, 2015. These applications are hereby incorporated by reference herein.

BACKGROUND

The following relates generally to the medical critical care arts, emergency medical care arts, cardiac diagnostic arts, electrocardiographic (ECG) arts, acute ischemia detection arts, and related arts.

BRIEF SUMMARY

In some illustrative embodiments disclosed herein, an acute ischemia detection device comprises a 12-lead electrocardiograph (ECG) device, an electronic data processing device, and a display component. The electronic data processing device is programmed to perform operations including: applying 12-lead ECG to vessel-specific lead (VSL) transforms to 12-lead ECG data acquired by the 12-lead ECG device to generate VSL lead data; determining ST values for the VSL lead data; and deciding whether the 12-lead ECG data acquired by the 12-lead ECG device indicates acute ischemia by comparing the ST values for the VSL lead data with VSL lead ST thresholds. The display component is configured to display an acute ischemia alarm or warning if the decision is the 12-lead ECG data acquired by the 12-lead ECG device indicates acute ischemia.

In some illustrative embodiments disclosed herein, an acute ischemia detection method comprises: acquiring 12-lead electrocardiograph (ECG) data for a subject; applying 12-lead ECG to vessel-specific lead (VSL) transforms to the 12-lead ECG data to generate VSL lead data for the subject; determining ST values for the VSL lead data; deciding whether the subject has acute ischemia by comparing the ST values for the VSL lead data with VSL lead ST thresholds; and issuing an acute ischemia alarm or warning if the decision is that the subject has acute ischemia.

In some illustrative embodiments disclosed herein, an electrocardiograph device includes a 12-lead electrocardiograph (ECG) device and an electronic data processing device programmed to perform operations including applying 12-lead ECG to vessel-specific lead (VSL) transforms to 12-lead ECG data acquired by the 12-lead ECG device to generate VSL lead data. The 12-lead ECG device may, for example, be configured to acquire 12-lead ECG data using at least one of (i) a standard 12-lead ECG electrode placement and (ii) a Mason-Likar 12-lead ECG electrode placement. The electrocardiograph device may further include a display component configured to display the generated VSL lead data as VSL lead traces.

One advantage resides in providing improved accuracy in interpreting the 12-lead ECG for acute ischemia identification.

Another advantage resides in providing 12-lead ECG-based acute ischemia detection with reduced false-negatives.

Another advantage resides in displaying derived vessel-specific lead (VSL) ECG traces in a lead-trace output format familiar to clinicians.

Another advantage resides in providing 12-lead ECG-based acute ischemia detection tailored for the specific lead placement (e.g. standard 12-lead ECG electrode placement or Mason-Likar 12-lead electrode placement) and/or tailored to subject gender.

Still further advantages of the present invention will be appreciated to those of ordinary skill in the art upon reading and understand the following detailed description. It will be appreciated that a given embodiment may provide none, one, two, or more of these advantages.

DETAILED DESCRIPTION

Figure 1:
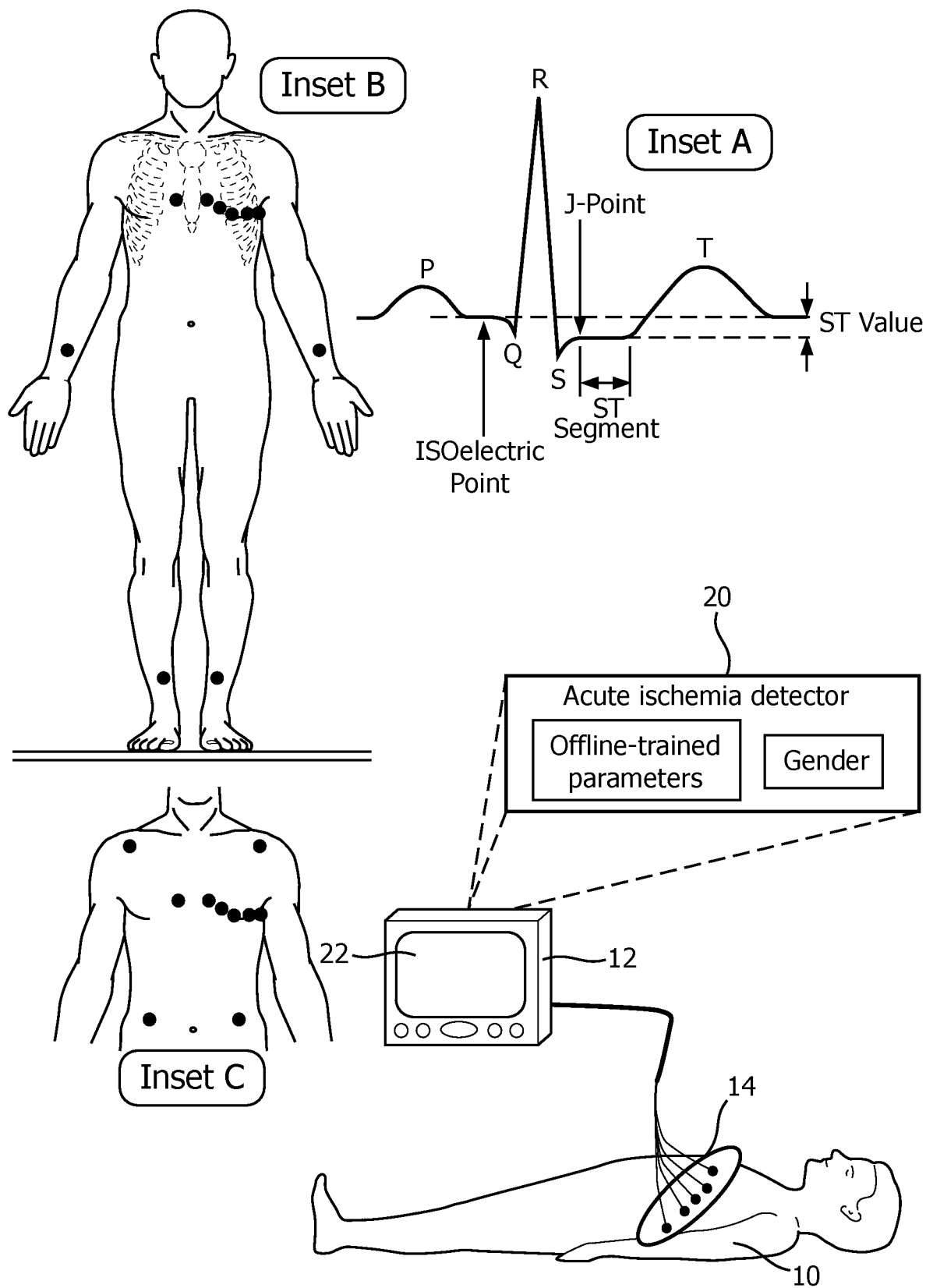
FIG. 1 diagrammatically shows an electrocardiogram (ECG)-based acute ischemia detection system. Inset A shows a typical ECG with some salient features labeled. Inset B shows a standard 12-lead ECG electrode configuration suitably used in the detection system, while Inset C shows an alternative Mason-Likar ECG electrode configuration alternatively used in the detection system.

The electrocardiogram (ECG) is a graphic recording of the electrical potentials generated by the electrical activity in the heart. The ECG may be recorded physically, e.g. on paper, or electronically as a data file, for example storing time-stamped voltage samples acquired across ECG electrodes. The electrical impulse formation and conduction associated with each cardiac contraction produces weak electrical currents that spread through the entire body. By applying electrodes to various positions on the body and connecting these electrodes to an electrocardiographic (ECG) apparatus, the variation in the magnitude of the electrical potential is recorded. The magnitude of the recorded ECG is usually in the order of millivolts. A typical ECG, as shown in FIG. 1: Inset A, comprises a series of waves, which are repeated with each cardiac cycle. These waves are labelled as P, QRS, and T according to convention. The P-wave represents the depolarization and contraction of both atria, the QRS complex represents the depolarization and contraction of the ventricles, and the T-wave represents the repolarization of the ventricles.

In a standard 12-lead ECG as shown in FIG. 1: Inset B, ten electrodes are used: three are placed on the right arm (RA), left arm (LA), and left leg (LL), and six are placed on the chest (V1 to V6), and a ground reference electrode is placed on the right leg (RL), although more generally it could be placed anywhere. In order to obtain a specific precordial lead, a chest electrode must be placed in the exact appropriate location.

The 12 ECG leads, consisting of three limb leads (I, II, and III), three augmented limb leads (aVR, aVL, and aVF), and six precordial leads (V1 to V6), are derived from the nine electrodes as shown in Table 1. Each of the three limb leads represents a difference of electrical potential between two selected sites. Each of the three augmented limb leads records the electrical potential at one extremity with reference to the other two remaining extremities. These six limb leads record the electrical potentials in the frontal plane. The six frontal plane leads are not independent. In fact, there are only two independent signal channels from three limb electrodes.

TABLE 1

Standard 12-lead ECG

| Lead | Type | Lead Calculation |
| --- | --- | --- |
| I | Limb | LA − RA |
| II | Limb | LL − RA |
| III | Limb | LL − LA |
| aVR | Augmented | RA − (LA + LL)/2 |
| aVL | Augmented | LA − (RA + LL)/2 |
| aVF | Augmented | LL − (RA + LA)/2 |
| V1 | Precordial | V1 − (RA + LA + LL)/3 |
| V2 | Precordial | V2 − (RA + LA + LL)/3 |
| V3 | Precordial | V3 − (RA + LA + LL)/3 |
| V4 | Precordial | V4 − (RA + LA + LL)/3 |
| V5 | Precordial | V5 − (RA + LA + LL)/3 |
| V6 | Precordial | V6 − (RA + LA + LL)/3 |

The precordial V leads record the electrical potential at the specific chest locations with reference to the three extremities. Each precordial lead records the electrical potential in the horizontal plane as viewed from the selected electrode placement site. In addition to the six standard chest leads, additional chest leads are often used in the investigation of ischemia. They include 4 right-side chest leads (V3R, V4R, V5R, and V6R) and 3 posterior leads (V7, V8, and V9).

Although the placement of the standard limb electrodes (FIG. 1: Inset B) is not a problem for acquiring resting 12-lead ECG, it can be impractical for ambulatory applications such as continuous monitoring or exercise testing. Not only it is inconvenient and uncomfortable for the patient, the limb electrodes are also susceptible to movement artifacts. Therefore, for ambulatory applications, a modified electrode configuration (Mason-Likar) is often used. This Mason-Likar configuration is shown in FIG. 1: Inset C. In the Mason-Likar 12-lead ECG configuration, the three limb electrodes and the ground electrode are placed on the torso as shown in FIG. 1: Inset C.

The term myocardial ischemia refers to a reduction in the supply of blood to the muscle cells of the heart. This occurs when the arterial conduit becomes limited in its ability to feed tissues with oxygen sufficient to meet their metabolic requirements. The main cause of myocardial ischemia is coronary artery disease. The effects of ischemia are reversible if the episode is limited in time.

When a myocardial ischemia episode remains unrelieved, tissue cells begin to die and a myocardial infarction is the result.

After ventricular depolarization, normal myocardial cells are at nearly the same potential. Therefore in the absence of any cardiac pathology, the end of depolarization and the beginning of repolarization are normally isoelectric. On the ECG signal, this region is called the ST segment. It is defined as the region between the end of the S-wave, also called the J-point, and the beginning of the T-wave (see FIG. 1: Inset A). Ischemic and damaged tissue causes the cells of the myocardium to become either more or less excitable. This abnormal electrical characteristic change is most apparent in the repolarization phase. Since the ST segment of the ECG primarily reflects ventricular repolarization, the ischemia or cell damage is displayed as changes (depression or elevation) in the level of the ST segment.

The location of the ECG electrodes and the direction and magnitude of the ST change indicate the area of the heart at risk, and the possible extent of the damage. The probability of detecting ischemic episodes, and locating them, increases with the number of ECG leads employed, the appropriate choice of ECG leads, and correct lead placement.

A standard approach for determining the ST segment measurement is by measuring the voltage difference between the value at the J-point or a point 60 or 80 milliseconds (ms) after the J-point and the isoelectric baseline (see FIG. 1: Inset A). The isoelectric baseline is either between the P- and Q-waves (the P-R interval) or in front of the P-wave (the T-P interval). ST segment measurement values can be reported in millivolt (mV), microvolt (uV) or millimeter (mm). Because standard (paper output) ECG strips are normally plotted at a scale of 10 mm per 1 mV, it follows that 1 mm ST segment change represents a voltage change of 0.1 mV. A positive value represents an ST elevation, and a negative value represents an ST depression. ST segment changes of greater than 1 mm (or 0.1 mV) are generally considered significant.

Some conventional terminology employed in literature discussion of acute myocardial infarction (AMI) and acute coronary syndrome (ACS) is next described. ACS refers to three types of coronary artery disease that are associated with sudden rupture of plaque inside the coronary artery. Types of ACS include: unstable angina (UA); non-ST segment elevation myocardial infarction (NSTEMI); and ST segment elevation myocardial infarction (STEMI). The location of the blockage, the length of time that blood flow is blocked and the amount of damage that occurs determines the type of acute coronary syndrome. Myocardial infarction (MI) is a major cause of death and disability worldwide. In the United States alone, more than one million hospitalizations are required for ACS of which more than half are for acute myocardial infarction (AMI) including roughly two-thirds with NSTEMI and the rest with STEMI.

According to the current consensus document (Thygesen et al., Joint ESC/ACCF/AHA/WHF Task Force for the Redefinition of Myocardial Infarction. Universal definition of myocardial infarction. J Am Coll Cardiol 2007; 50:2173-95) from the European Society of Cardiology (ESC)/American College of Cardiology Foundation (ACCF)/American Heart Association (AHA)/World Heart Federation (WHF), the STEMI criteria for the standard 12-lead ECG are: ST elevations measured at the J-point in two contiguous leads with value ≥0.2 mV (or 2 mm) in men, or ≥0.15 mV (or 1.5 mm) in women in leads V2, V3 and/or ≥0.1 mV (or 1 mm) in other 10 leads. The 10 contiguous lead pairs are: (aVL, I), (I, −aVR), (−aVR, II), (II, aVF), (aVF, III), (V1, V2), (V2, V3), (V3, V4), (V4, V5), (V5, V6). Criteria for right-side and posterior leads are provided in the AHA/ACCF/HRS Scientific Statement document (Wagner et al., AHA/ACCF/HRS Recommendations for the Standardization and Interpretation of the Electrocardiogram Part VI: Acute Ischemia/Infraction. Circulation 2009; 119:e262-e270).

Current practice guidelines for managing patients with AMI are aimed to optimize care and outcome for these patients. For the STEMI patients, since the infarct-related artery is usually totally occluded, the treatment goal is to obtain normal coronary blood flow and interrupt the infarction as rapidly as possible. Effective reperfusion treatment options include intravenous thrombolytic therapy and percutaneous coronary intervention (PCI). Specifically, the current treatment guidelines for the STEMI patients are: (1) for hospital with PCI capability treat with primary PCI within 90 minutes or first medical contact, and (2) for hospital without PCI capability treat with fibrinolytic therapy within 30 minutes of hospital presentation unless fibrinolytic therapy is contraindicated. Regardless of the mode of reperfusion, the overarching concept is to minimize total ischemic time, which is defined as the time from onset of symptoms of STEMI to initiation of reperfusion.

To effectively managing STEMI patients to achieve the stated treatment goals a rapid and accurate diagnosis (AMI detection) is essential. Because biochemical markers of AMI may not rise immediately after the onset of symptoms, the initial diagnosis and decision of reperfusion treatment are often based on clinical symptoms and the standard 12-lead ECG. However, in patients with symptoms suggesting ACS, currently used diagnostic criteria based on the 12-lead ECG identify STEMI patients with high specificity but low sensitivity. In one study (2005 International Consensus Conference Part 5: Acute Coronary Syndromes. Circulation 2005; 112:III55-III72), using admission 12-lead ECGs emergency physicians blinded to biomarker results established the diagnosis of STEMI with a low sensitivity of 42% (95% CI, 32%-52%), although specificity is high at 99.7% (95% CI, 98%-99.9%). Consequently, many false-negative patients may not receive the optimal therapy and its potential benefit.

One reason for the low sensitivity is that large areas of the thoracic surface are not sampled with the six precordial leads (V1 to V6) placed in the pre-specified locations in the standard 12-lead ECG. In view of this, ECG diagnosis of AMI could potentially be optimized by adding posterior thoracic and/or right-sided precordial leads; or by recording electrical potentials using lead arrays around the torso, termed body surface potential mapping (BSPM). In one study (Ornato et al., Body surface mapping vs 12-lead electrocardiography to detect ST-elevation myocardial infarction. Am J Emerg Med 2009; 27(7):779-784), an 80-lead mapping system was used to improve the detection of STEMI patients. In another study (Kornreich et al., Body surface potential mapping of ST segment changes in acute myocardial infarction. Circulation 1993; 87:773-782), based on the 120-lead discriminant maps, obtained by subtracting the averaged map of normal subjects from the averaged MI maps, two torso locations with the most significant changes on ST elevation and depression were identified for each of the three MI groups according to the region of infarction (anterior, inferior, and posterior). Of these six locations, five were not covered by the standard precordial lead locations. Improved performance was shown using stepwise discriminant analysis.

These studies demonstrate that adding additional electrodes have the potential to improve detection performance. However, clinical use of a large number of electrodes is challenging due to the extra cost, patient comfort, and time associated with obtaining these additional leads. Methods that require accurate placement of additional electrodes on non-standard locations on the torso can also be a major challenge for the clinicians. Still further, cardiologists are typically trained to interpret the ubiquitous conventional 12-lead ECG, and may be uncomfortable diagnosing based on alternative ECG electrode configurations.

Rather than acquiring additional leads directly, in another study (Horáček et al., "Optimal electrocardiographic leads for detecting acute myocardial ischemia", J Electrocardiol 2001; 34(Suppl):97-111), three vessel-specific leads (VSLs) with the most sensitive ST segment changes during acute ischemia were determined using 120-lead maps recorded during balloon angioplasty of left anterior descending (LAD) artery, right coronary artery (RCA), and left circumflex (LCX) artery. For each artery occlusion, the most elevated and depressed ST segment locations were identified using the averaged ΔST map. Each individual ΔST map was obtained by subtracting the baseline map (before balloon catheter insertion) from the map at peak balloon inflation. From the same 120-lead mapping dataset, three linear equations were used to derive the bipolar VSLs: RCA, LCX, and RCA, from the 12-lead ECG using the standard least-square method. Linear discriminant function was used as the classifier for STEMI detection.

A difficulty in applying this approach in an emergency clinical setting is that the analysis of ΔST requires the baseline ECG—but for ACS patients undergoing an acute cardiac event, the baseline ECGs are usually not available. Rather, clinical decisions in the emergency setting are typically based on reviewing the admission ECG only. Further, since the discriminant classifier is not transparent to the clinician, it is difficult for the clinician to independently verify the detection made by the system. Clinicians may prefer to know the detection thresholds on the VSLs and be able to make independent judgment similar to the currently used STEMI criteria.

In a follow-up study (Horáček et al., "Detection of myocardial ischemia by vessel-specific leads derived from the 12-lead electrocardiogram and its subsets", J Electrocardiol 2008; 41:508-517), an independent 120-lead BSPM Dalhousie Superset was used for deriving the three VSLs linear equations. An optimal single, gender-independent, detection threshold for all VSLs was also determined for acute ischemia detection. In the case of the STEMI criteria operating on conventional 12-lead ECG, ST changes have been found to be both gender- and lead-dependent.

Approaches disclosed herein improve the accuracy in interpreting the 12-lead ECG for acute ischemia identification. Test results presented herein evidence that the disclosed approaches improve the detection of STEMI patients (e.g., achieving higher sensitivity without sacrificing specificity) so these otherwise false-negative patients can also benefit from the optimal treatment therapy. The disclosed approaches incorporate various aspects as discussed hereinafter.

In some aspects, disclosed approaches use peak data directly to identify torso locations with maximum ST changes during AMI, instead of using ST changes from the patient's baseline ECG. In an emergency clinical setting, a baseline ECG is usually not available. Identifying the torso locations using peak data as disclosed herein is compatible with ECG data actually available in a typical emergency setting.

The most sensitive leads can be recorded directly as bipolar leads with electrodes placed at the optimal sites. However, in approaches disclosed herein these leads are derived from the conventional 12-lead ECG. Advantageously, no extra physical electrodes are employed beyond the familiar standard (or Mason-Likar) 12-lead ECG.

In embodiments disclosed herein, transformation coefficient sets for the VSLs are generated for both the standard and Mason-Likar electrode placements. In general, ECGs acquired due to different (standard v. Mason-Likar) 12-lead placement are not the same.

In addition to providing improved STEMI detection, the derived VSLs waveforms are also optionally provided for display and tracking of ST changes. This provides the clinician with a familiar lead-trace output format.

In some embodiments, instead of using discriminant function based classification, the detection thresholds are based on the ST levels of the VSLs directly. Together with the provided VSLs waveforms, clinicians can independently verify the detection of STEMI using the recommended detection thresholds.

Some embodiments disclosed herein use lead-specific thresholds rather than the same single threshold for all VSLs for further detection performance improvement. This approach accounts for the possibility that different ECG leads have difference amplitude, e.g. depending on their distance from the heart. For optimal detection performance the thresholds are optionally adjusted based on the signal strength.

Additionally or alternatively, derived VSLs can be scaled so that the same STEMI thresholds can be used for the VSL based AMI detection. For example, if a threshold of 110 uV (instead of 100 uV) produces a better detection performance for a given lead then the lead can be scaled down by dividing the signal (or ST measurement) by 1.1 so that 100 uV can be used as the threshold similar to some of values used in the STEMI criteria. In addition, it is also much easier for a clinician to visually check from a recorded ECG for a threshold of 100 uV than a threshold of 110 uV.

Furthermore, some embodiments disclosed herein employ gender-specific thresholds to reflect that ST changes for females tend to be less than for males. It is recognized herein that better performance can be realized if the detection thresholds are gender specific.

With reference again to FIG. 1, in illustrative embodiments disclosed herein, a subject 10, who is typically a patient being assessed in an emergency care setting such as an ambulance, an emergency room, an intensive care unit (ICU), cardiac care unit (CCU), or so forth, is monitored by a patient monitor 12 with ECG data acquisition capability (or, alternatively, by a dedicated ECG system; more generally, the device 12 may be any ECG device that provides 12-lead ECG based ST segment analysis for ischemia detection, such as a bedside monitor, cardiac defibrillator, cardiograph, stress testing system, telemetry monitor, or Holter monitor). To this end, a 12-lead ECG electrodes set 14 is operatively connected with the subject 10. The 12-lead electrodes set 14 may have a standard 12-lead configuration (Inset B) or a Mason-Likar 12-lead configuration (Inset C). It is also contemplated to employ the disclosed approach with other common lead configurations such as an EASI configuration, with suitable training on such a lead set as described herein, e.g. with reference to FIG. 2. The patient monitor 12 (or dedicated ECG system) comprises an electronic data processing device including a microprocessor, microcontroller, or the like, which executes software or firmware implementing an acute ischemia detector 20 which performs on-line operations disclosed herein (e.g. with reference to FIG. 3) employing certain offline-trained parameters (e.g. 12-lead-to-VSL transforms, VSL-specific thresholds, and optional VSL scaling factors) trained as disclosed herein (e.g. with reference to FIG. 2), some of which are optionally lead placement-specific (e.g. standard v. Mason-Likar) and/or gender-specific (so that the gender of the subject 10 is another input to the acute ischemia detector 20). The patient monitor 12 (or dedicated ECG system) includes a display component 22 via which the output of the acute ischemia detector 20 is displayed. In addition to, or possibly in place of, the illustrated display component 22, the output may be printed via a printer (not shown). This output may, for example, include an alarm or warning that is issued if acute ischemia is detected (additionally or alternatively, an audio alarm or warning may be issued). The output may optionally also include plots of vessel specific lead (VSL) traces generated by the acute ischemia detector from the 12-lead ECG. Additionally, the patient monitor 12 (or dedicated ECG system) may optionally display the 12-lead ECG lead traces (or selected ones of these 12-lead traces), and if the device is a multi-function patient monitor the patient monitor 12 may additionally or alternatively display other patient data (e.g. other physiological sensor data, e.g. blood pressure, $SpO_2$, et cetera), or so forth.

Figure 2:
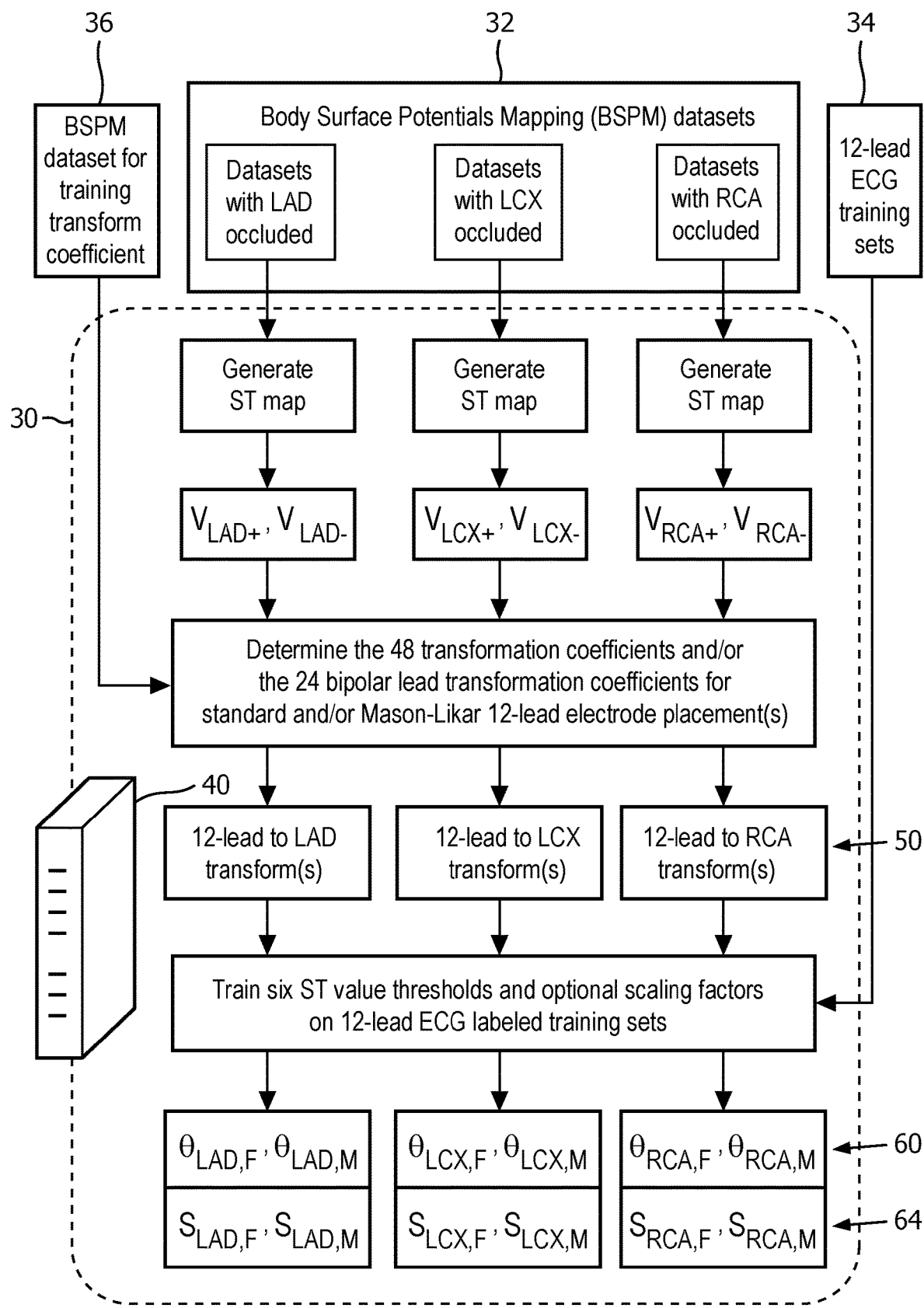
FIG. 2 diagrammatically illustrates an offline processing system for training offline-trained parameters used in the acute ischemia detection system of FIG. 1.

With brief reference to FIG. 2, the offline processing 30 entails substantial computational load, e.g. data processing performed on a collection of body surface potential mapping (BSPM) data sets 32, where each BSPM includes (for example) data for 120 leads acquired of a subject with various coronary arteries blocked, and further optimizing VSL-specific thresholds for a training set of 12-lead ECG data sets 34. In view of this substantial computational load, the offline processing 30 is suitably performed by a sufficiently powerful electronic data processing device 40 (diagrammatically indicated in FIG. 2), such as a desktop computer, a network-based server computer, a computing cluster, a cloud computing resource, or so forth.

Figure 3:
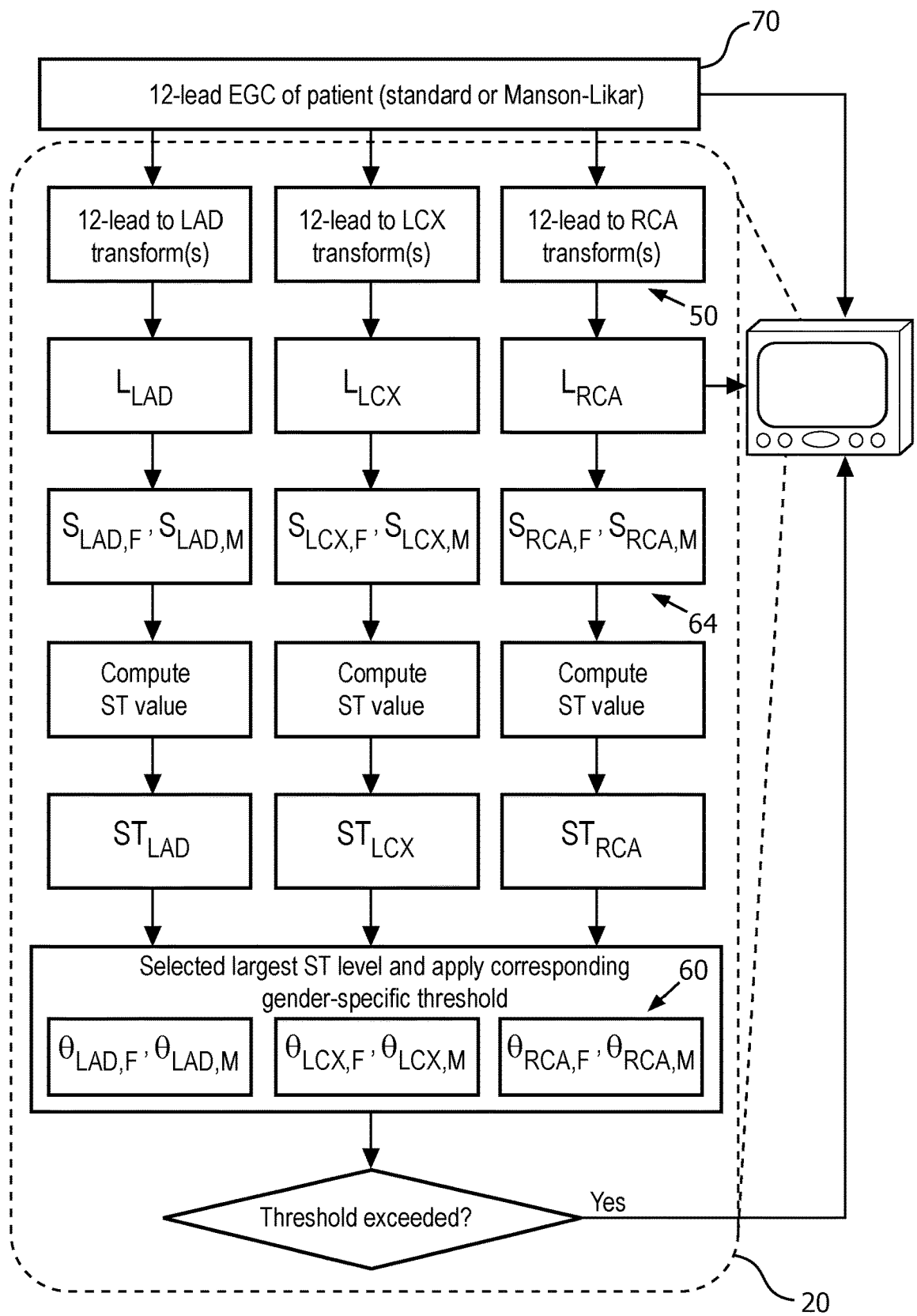
FIG. 3 diagrammatically illustrates online processing suitably performed by the acute ischemia detection system of FIG. 1.

It will also be appreciated that the acute ischemia detector 20 of FIGS. 1 and 3 may be embodied as a non-transitory storage medium storing software or firmware executable by the patient monitor 12, dedicated ECG, or other electronic data processing device to perform the disclosed online acute ischemia detector processing. Similarly, the offline processing 30 of FIG. 2 may be embodied as a non-transitory storage medium storing software or firmware executable by the computer or other electronic data processing device 40 to perform the disclosed offline processing 30. The non-transitory storage medium may, for example, comprise a hard disk drive, RAID disk array, or other magnetic storage medium, and/or a read-only memory (ROM), flash memory, or other electronic storage medium, and/or an optical disk or other optical storage medium, or so forth.

Approaches disclosed herein improve acute ischemia detection performance as compared with the currently used STEMI criteria by using criteria based on 3 vessel-specific leads (VSLs) derived from the 12-lead ECG. In the illustrative embodiments, off-line processing 30 is employed to generate 12-lead ECG-to-VSL leads transforms 50, ST threshold(s) 60, and optional lead scaling factors 64 (see FIG. 2), which are then used during on-line processing of a particular patient performed by the acute ischemia detector 20 to diagnose acute ischemia (see FIG. 3).

In one embodiment, the off-line processing 30 includes the following. The locations on the body surface are determined with the largest ST elevation and depression during occlusion of each of the three main coronary arteries LAD, LCX, and RCA. Body surface potential mapping (BSPM) data 32 obtained during balloon-inflation percutaneous coronary intervention (PCI) procedure and/or acute myocardial infarction (AMI) are suitably used in carrying out this task. To this end, one or more BSPM datasets with LAD occluded are provided to determine the optimal LAD-specific location; one or more BSPM datasets with LCX occluded are provided to determine the optimal LCX-specific location;

and one or more BSPM datasets with RCA occluded are provided to determine the optimal RCA-specific location. The transformation coefficients are generated for the three linear equations (or, more generally, transforms) 50 used for deriving the VSLs from the 12-lead ECG using the least-square method. A BSPM dataset 36 is employed to produce a robust coefficient set. Additional 12-lead acute ischemia datasets 34 are used to determine the optimal acute ischemia detection thresholds 60 for the VSLs. Suitable performance measures for this optimization include detection sensitivity and specificity. In one approach, improved performance is measured as higher detection sensitivity with no loss of the high detection specificity as achieved by the STEMI criteria currently used in clinical practice.

The foregoing processing 30 is done off-line (that is, before the acute ischemia detector 20 is applied, e.g. using the illustrative computer 40). For the online analysis performed by the acute ischemia detector 20, the information required from the off-line analysis 30 is suitably pre-stored in the patient monitor 12. These information include the following: the transforms 50, the thresholds 60, and the optional scaling factors 64. The transforms 50 are suitably represented in one embodiment by two sets of transformation coefficients for deriving the three vessel-specific leads: LAD, LCX, and RCA. One set of transform coefficients is for standard 12-lead ECG electrodes placement, and the other set of transform coefficients is for the Mason-Likar 12-lead ECG electrodes placement. Each coefficient set contains 24 coefficients (8 coefficients per lead for 3 leads). In the illustrative embodiment, the thresholds 60 include six detection thresholds, namely two gender-specific thresholds per VSL, with three VSLs (LAD, LCX, and RCA).

With reference to FIG. 3, the illustrative on-line analysis performed by the acute ischemia detector 20 operates on 12-lead ECG data 70 acquired for the subject 10 being diagnosed. The online analysis includes the following. Three VSLs are derived from the three linear equations (or transforms) 50 using the 24-coefficient set (generated by the offline processing 30) and the eight input ECG leads (II, III, V1, . . . , V6) of the ECG data 70 acquired for the subject 10. (The appropriate coefficients are used depending upon whether the subject ECG 70 is acquired using a standard or Mason-Likar 12-lead configuration). In some embodiments, the derived VSL signals may optionally be scaled by the scaling factors 64. ST measurements for the three VSLs is then performed, for example using an available ST measurement algorithm of the patient monitor 12 (or dedicated ECG system) that is already provided to perform ST measurements on 12-lead ECG data. The same equations can also be used for deriving the ST measurements for the VSLs directly if ST measurements for the 8 input ECG leads are provided. The three VSL ST measurements ($ST_{LAD}$, $ST_{LCX}$, and $ST_{RCA}$ for the LAD, LCX, and RCA leads, respectively) are then checked against the pre-stored thresholds 60. Acute ischemia detection is declared if any VSL exceeds the gender- and lead-specific threshold.

Having provided an overview of the disclosed acute ischemia detection techniques with reference to FIGS. 1-3, some more specific illustrative examples are next described, starting with illustrative examples of the offline processing 30 of FIG. 2.

The six torso locations for the three bipolar VSLs are determined as follows. First, determine the locations on the body surface with the largest ST elevation and depression during occlusion of each of the three main coronary arteries LAD, LCX, and RCA. The most elevated and depressed torso locations for LAD, LCX, and RCA are $V_{LAD+}$ and $V_{LAD-}$, $V_{LCX+}$ and $V_{LCX-}$, and $V_{RCA+}$ and $V_{RCA-}$, respectively. To this end, the BSPM datasets 32 acquired during balloon-inflation PCI procedure and/or AMI are used. In an actually-performed example, a 120-lead ECG mapping dataset recorded at Dalhousie University during acute ischemic episodes induced by elective balloon-inflation PCI procedure of left anterior descending coronary artery (LAD; n=32), right coronary artery (RCA; n=36), and left circumflex coronary artery (LCx; n=23) (see Horáček et al., "Optimal electrocardiographic leads for detecting acute myocardial ischemia", J Electrocardiol 2001; 34(Suppl):97-111) was used for identifying the 6 optimal torso sites. The mean peak inflation map for each artery occlusion was obtained by averaging 15 patients in each group with the largest ST changes. From these three ST maps the torso locations for the six VSLs were determined.

Next, the transformation coefficients are determined for deriving the VSLs using the following linear transformation Equation (1):

$$\begin{bmatrix} V_{LAD+} \\ V_{LAD-} \\ V_{LCX+} \\ V_{LCX-} \\ V_{RCA+} \\ V_{RCA-} \end{bmatrix} = \begin{bmatrix} C_{11} & C_{12} & C_{13} & C_{14} & C_{15} & C_{16} & C_{17} & C_{18} \\ C_{21} & C_{22} & C_{23} & C_{24} & C_{25} & C_{26} & C_{27} & C_{28} \\ C_{31} & C_{32} & C_{33} & C_{34} & C_{35} & C_{36} & C_{37} & C_{38} \\ C_{41} & C_{42} & C_{43} & C_{44} & C_{45} & C_{46} & C_{47} & C_{48} \\ C_{51} & C_{52} & C_{53} & C_{54} & C_{55} & C_{56} & C_{57} & C_{58} \\ C_{61} & C_{62} & C_{63} & C_{64} & C_{65} & C_{66} & C_{67} & C_{68} \end{bmatrix} \times \begin{bmatrix} II \\ III \\ V1 \\ V2 \\ V3 \\ V4 \\ V5 \\ V6 \end{bmatrix} \quad (1)$$

In Equation (1), the six torso locations for the VSLs form the leftmost 6×1 column vector. The 8 independent ECG leads (II, III, V1, . . . , V6) from the 12-lead ECG form the rightmost 8×1 vector of Equation (1). The 48 transformation coefficients $C_{ij}$, i=1, . . . , 6 and j=1, . . . , 8 form the 6×8 transformation matrix C of Equation (1). To determine the transformation coefficients listed in Equation (1), a large BSPM dataset is employed. As an example, in one actually performed determination a Dalhousie 120-lead mapping Superset (n=892) (see Horáček et al., "On designing and testing transformations for derivation of standard 12-lead/18-lead electrocardiograms and vectorcardiograms from reduced sets of predictor leads", J Electrocardiol 2008; 41:220-229) was used to derive the transformation coefficients using standard least-square regression method. The estimates of $C_{ij}$, i=1, . . . , 6 and j=1, . . . , 8 were chosen to minimize the error sum of squares over all available data samples of the QT interval for all subjects of the Superset using a general-purpose procedure for regression as described in Horáček et al., supra.

In some embodiments, two separate sets of transformation coefficients are derived: one for the standard 12-lead placement, and one for Mason-Likar 12-lead placement. More generally, transforms for other lead placements could be similarly be determined. Moreover, while Equation (1) employs a linear transform, other 12-lead-to-VSL transform topologies are also contemplated.

Next, the three VSLs are obtained. The three vessel-specific bipolar leads for LAD, LCX, and RCA can be calculated as the difference between the positive and negative terminals as shown in Equation (2):

$$\begin{bmatrix} L_{LAD} \\ L_{LCX} \\ L_{RCA} \end{bmatrix} = \begin{bmatrix} V_{LAD+} \\ V_{LCX+} \\ V_{RCA+} \end{bmatrix} - \begin{bmatrix} V_{LAD-} \\ V_{LCX-} \\ V_{RCA-} \end{bmatrix} \quad (2)$$

Alternatively, if leads at positive and negative terminals are not needed, the three vessel-specific leads can be directly calculated using the following Equation (3):

$$\begin{bmatrix} L_{LAD} \\ L_{LCX} \\ L_{RCA} \end{bmatrix} = \begin{bmatrix} T_{11} & T_{12} & T_{13} & T_{14} & T_{15} & T_{16} & T_{17} & T_{18} \\ T_{21} & T_{22} & T_{23} & T_{24} & T_{25} & T_{26} & T_{27} & T_{28} \\ T_{31} & T_{32} & T_{33} & T_{34} & T_{35} & T_{36} & T_{37} & T_{38} \end{bmatrix} \times \begin{bmatrix} II \\ III \\ V1 \\ V2 \\ V3 \\ V4 \\ V5 \\ V6 \end{bmatrix} \quad (3)$$

The transformation matrix T of Equation (3) is a 3×8 matrix with a total of 24 elements $T_{ij}$, i=1, 2, 3 and j=1, ..., 8. In another approach, the transformation coefficients $T_{ij}$ can be obtained from $C_{ij}$ of Equation (1) using the following Equation (4):

$$T_{ij} = C_{2i-1,j} - C_{2i,j} \quad i=1,2,3; j=1,\ldots,8 \quad (4)$$

Alternatively, the coefficients $T_{ij}$ can be directly calculated the same as the coefficients $C_{ij}$ in Eq. (1) as described with reference to Equation (1).

Note also that Equations (2) and (3) can be used to calculate both the ECG waveforms for each input ECG sample as well as the ST values for the VSLs.

The thresholds 60 for detecting acute ischemia are optimized in this example as follows. The maximum value of the three vessel-specific leads is identified, i.e.:

$$ST_{MaxVSL} = \text{Max}\{ST_{LAD}, ST_{LCX}, ST_{RCA}\} \quad (5)$$

where $ST_{LAD}$, $ST_{LCX}$, and $ST_{RCA}$ are the ST values for the vessel-specific leads LAD, LCX, and RCA, respectively.

Detection of acute ischemia is determined by comparing the maximum ST value of the vessel-specific lead using six gender- and lead-specific thresholds $\theta_{i,j}$, i=LAD, LCX, or RCA, and j=female, or male using the following Expressions (6)-(8):

If $ST_{MaxVSL} =$ (6)

$$ST_{LAD} \text{ Positive detection if } ST_{LAD} > \begin{cases} \theta_{LAD,F} & \text{for female} \\ \theta_{LAD,M} & \text{for male} \end{cases}$$

If $ST_{MaxVSL} =$ (7)

$$ST_{LCX} \text{ Positive detection if } ST_{LCX} > \begin{cases} \theta_{LCX,F} & \text{for female} \\ \theta_{LCX,M} & \text{for male} \end{cases}$$

If $ST_{MaxVSL} =$ (8)

$$ST_{RCA} \text{ Positive detection if } ST_{RCA} > \begin{cases} \theta_{RCA,F} & \text{for female} \\ \theta_{RCA,M} & \text{for male} \end{cases}$$

To determine the optimal detection thresholds, the 12-lead acute ischemia datasets 34 are employed. These datasets 34 are suitably labeled as to whether each dataset is for a subject with acute ischemia, or without acute ischemia. Suitable performance measures are detection sensitivity and specificity. Improved performance may be measured as higher detection sensitivity with no loss of the high detection specificity as achieved by the STEMI criteria currently used in clinical practice.

An actually performed thresholds optimization used the STAFF III dataset (see Horáček et al., "Detection of myocardial ischemia by vessel-specific leads derived from the 12-lead electrocardiogram and its subsets", J Electrocardiol 2008; 41:508-517) which consists of 99 patients with single-vessel disease underwent elective coronary balloon angioplasty including LAD (n=35), RCA (n=47), and LCX (n=17). Standard 12-lead ECG was recorded continuously during prolonged balloon inflation (mean=5'27", range: 1'30"-7'17") and ST-segment was measured at the J point. To measure detection performance in terms of sensitivity and specificity, the baseline state (before catheter insertion) is considered (i.e. labeled) as the "non-ischemic" state and the end of the inflation is considered (i.e. labeled) as the "ischemic" state.

Another actually performed thresholds optimization used the Glasgow AMI dataset (see Martin et al., "ST-segment deviation analysis of the admission 12-lead electrocardiogram as an aid to early diagnosis of MI", JACC 2007; 50:1021-1028) which consists of 116 ACS patients with admission 12-lead ECG. AMI was confirmed with contrast-enhanced MM in 58 patients. ST segment measurements at J point are available for analysis.

Optionally, the VSLs are scaled. In one approach, normalized VSLs are computed as shown in Equation (9) for the LAD lead:

$$L_{LAD} = \begin{cases} L_{LAD}/S_{LAD,F} & \text{for female} \\ L_{LAD}/S_{LAD,M} & \text{for male} \end{cases} \quad (9)$$

and as shown in Equation (10) for the LCX lead:

$$L_{LCX} = \begin{cases} L_{LCX}/S_{LCX,F} & \text{for female} \\ L_{LCX}/S_{LCX,M} & \text{for male} \end{cases} \quad (10)$$

and as shown in Equation (11) for the RCA lead:

$$L_{RCA} = \begin{cases} L_{RCA}/S_{RCA,F} & \text{for female} \\ L_{RCA}/S_{RCA,M} & \text{for male} \end{cases} \quad (11)$$

In Equations (9)-(11), the scale factors $S_{ij}$, i=LAD, LCX, or RCA, and j=female, or male, are used to scale the VSLs so that the same threshold values (200, 150, and 100 uV) used for the STEMI criteria can also be used for the scaled VSLs. $S_{i,j}=1.0$ if no scaling is required. For example, if 210 uV is determined to be the optimal threshold for one of the VSLs, then the lead can be scaled down by a factor of 1.05. After the lead is scaled, then the optimal threshold value will be 200 uV to match one of the STEMI thresholds. The scaling factors are determined only after the optimal thresholds are determined.

Figure 4:
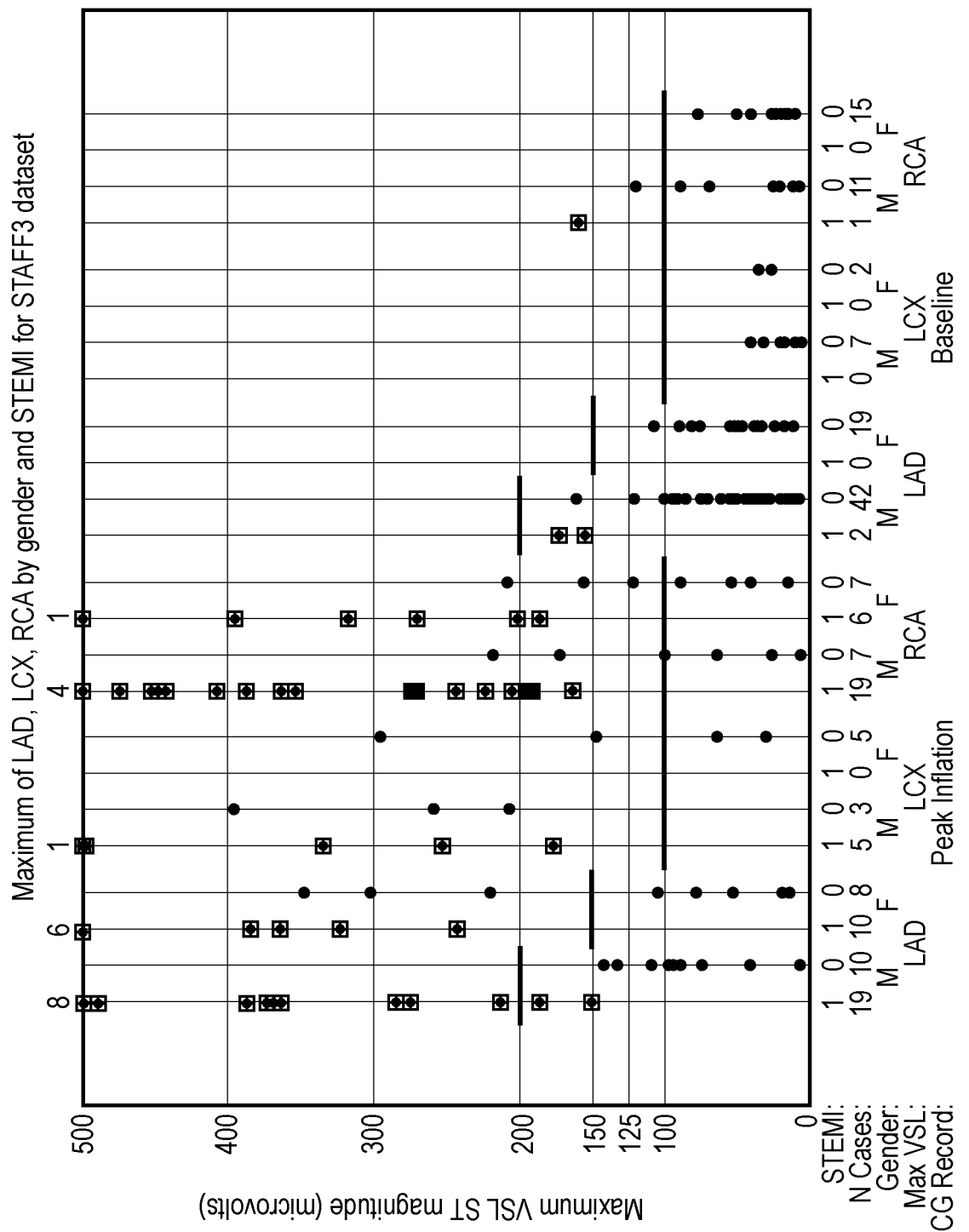
FIGS. 4 and 5 present results as described herein for offline processing performed in accordance with the offline processing system of FIG. 2.
Figure 5:
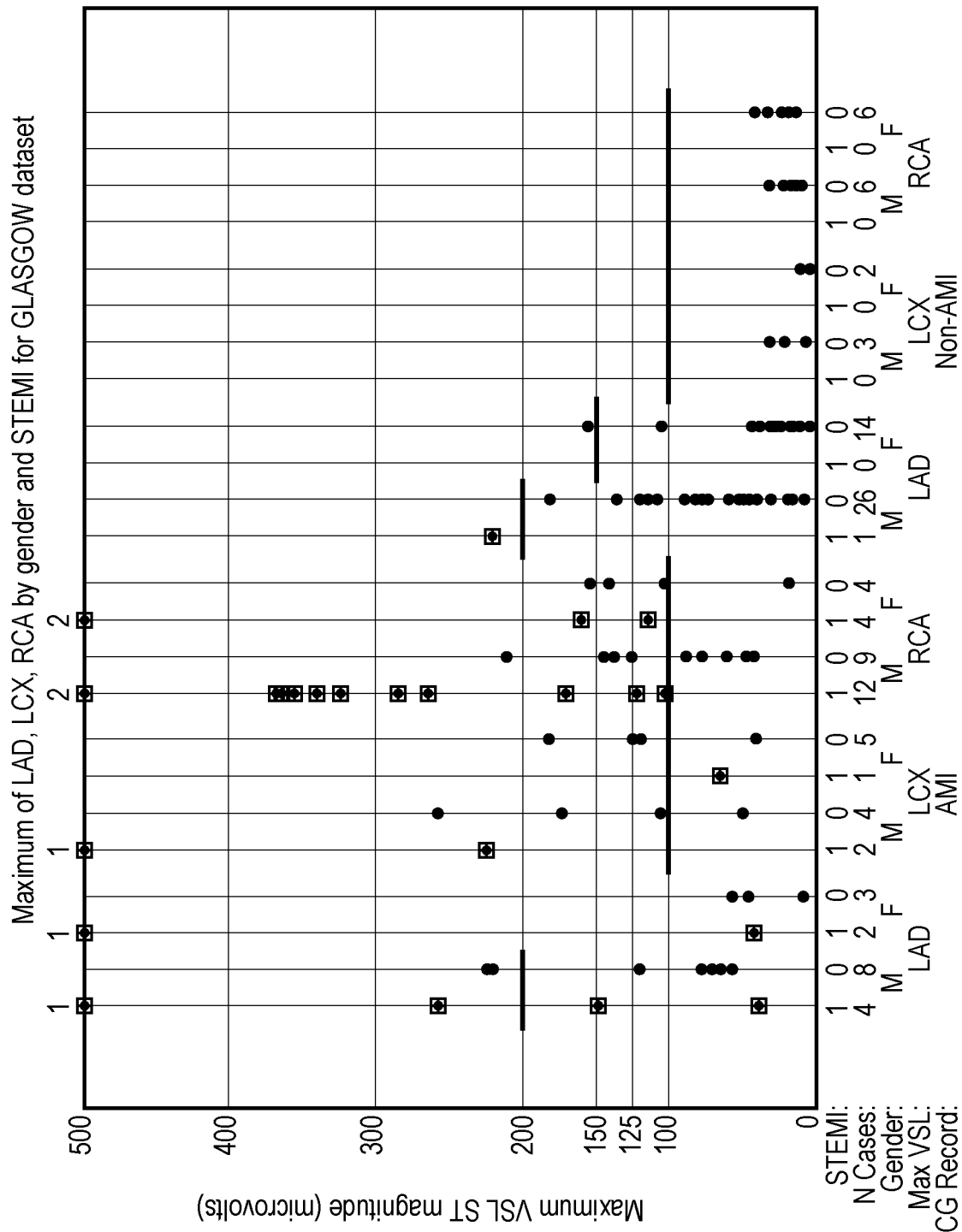

In the following, performance results are presented for actually performed offline processing, which are based on the transformation coefficients derived from the example datasets as described above. The performance results on the selected example datasets are shown in FIGS. 4 and 5 for the STAFF III dataset and the Glasgow dataset, respectively. In FIG. 4, the peak inflation results are plotted on the left-hand side and the baseline results are plotted on the right-hand sides. Similarly, in FIG. 5, the AMI results are presented on the left-hand side and the non-AMI results are shown on the right-hand sides.

For each ECG record the maximum ST value from the three VSLs is plotted as a data point according to the ST magnitude in uV as indicated on the y-axis. The data points are grouped according to the VSL associated with the maximum ST value. The first group is LAD and followed by LCX and RCA. Within each lead group there are four subgroups: 1) STEMI positive and Male, 2) STEMI negative and Male, 3) STEMI positive and Female, and 4) STEMI negative and Female. For data that met the current STEMI criteria a square box is added to the data point for better visualization. For data with values greater than 500 uV, a data point is plotted at 500 uV and a number is provided to indicate the actual count of data points that are above 500 uV. The short horizontal lines plotted represent the equivalent STEMI criteria: 200 uV for LAD Male, 150 uV for LAD Female, and 100 uV for RCA and LCX all gender.

Data points above the thresholds on the left panel are counted as true positive (TP) and data points above the thresholds on the right panel are counted as false positive (FP). The sensitivity and specificity performance results for several sets of thresholds are summarized in Table 2. The corresponding threshold values are listed in Table 3.

TABLE 2

Performance summary of STEMI vs. VSLs

| | Dataset | | | |
| --- | --- | --- | --- | --- |
| | STAFF3 PTCA | | Glasgow AMI | |
| Detection Method | Peak inflation (n = 99) Sensitivity | Baseline ECG (n = 99) Specificity | AMI (n = 58) Sensitivity | No AMI (n = 58) Specificity |
| STEMI | 60% (59/99) | 97% (96/99) | 43% (25/58) | 98% (57/58) |
| VSL | 74% (73/99) | 97% (96/99) | 62% (36/58) | 97% (56/58) |
| VSL+ | 74% (73/99) | 97% (96/99) | 62% (36/58) | 98% (57/58) |
| VSL++ | 72% (71/99) | 98% (97/99) | 60% (35/58) | 98% (57/58) |

TABLE 3

Detection thresholds for STEMI and VSLs

| Detection | Threshold (uV) | | |
| --- | --- | --- | --- |
| Criteria | LAD (M/F) | LCX (M/F) | RCA (M/F) |
| STEMI | 200/150 | 100/100 | 100/100 |
| VSL | 200/150 | 100/100 | 100/100 |
| VSL+ | 200/160 | 100/100 | 100/100 |
| VSL++ | 210/160 | 105/100 | 105/100 |

From Table 2, it is seen that using STEMI equivalent thresholds for VSLs based acute ischemia detection, VSLs had higher sensitivity than STEMI for both datasets while maintaining the same specificity for the STAFF III dataset. However, VSLs had one more false positive than STEMI (2 for VSLs and 1 for STEMI). This extra false positive detection can be removed by increasing the female LAD threshold from 150 to 160 uV. This setting is marked as VSL+. Note that this setting had no impact on detection sensitivity. To further demonstrate that the detection sensitivity will remain high with even higher thresholds, the male-specific thresholds for all leads were increased by 5%. This setting is labelled as VSL++ and listed in Table 3. The sensitivity and specificity for this setting are shown in Table 2. Note that for the STAFF III dataset there were two more false negatives and one less false positive. For the Glasgow dataset there was one more false negative and no change on false positive number. However, for both datasets, even with higher thresholds the sensitivity numbers were still significantly better than the STEMI numbers.

Assuming VSL++ were to be used, the scaling factors described in Equations (9)-(11) can then be calculated. The ST values are scaled down so that the same thresholds used in the STEMI criteria can be used for the VSLs for acute ischemia detection.

The test results summarized in Table 2 illustrate that the disclosed approach based on VSLs derived from the 12-lead ECG can identify acute myocardial ischemia in any vessel with better diagnostic performance than existing ACC/ESC STEMI criteria applied to the same 12 standard leads. At threshold values similar to those used for the STEMI criteria the specificity of the VSLs remained high while the sensitivity increased by significant amount compared to the numbers achieved by the currently used STEMI criteria for both datasets. In real clinical application, this increased sensitivity with no decrease of specificity will allows more acute MI patients to be correctly identified for acute therapy currently provided only for the STEMI patients.

The operations used for on-line analysis are described in the following.

The input information for the online acute ischemia detection analysis include: (1) 12-lead ECG electrode placement—Standard placement or Mason-Likar placement (if the 12-lead type is not provided then a pre-configured unit default setting may be used); (2) Patient gender—Male or female (if not provided then a pre-configured default gender setting may be used, which may be chosen as "male" to provide higher specificity, or "female" to provide higher sensitivity); and (3) 12-lead ECG waveforms and/or 12-lead ST measurements.

Step 1: (a) From the input 12-lead ECG, compute $V_{LAD+}$, $V_{LAD-}$, $V_{LCX+}$, $V_{LCX-}$, $V_{RCA+}$, and $V_{RCA-}$ using Equation (1) with pre-stored coefficient set C based on the specified 12-lead electrode placement; and (b) From the input 12-lead ST measurements, compute the ST values for these leads using the same coefficient set and Equation (1).

Step 2: (a) The three VSLs: $L_{LAD}$, $L_{LCX}$, and $L_{RCA}$ are computed using either Equation (2) with results from Step 1.a or Equation (3) from the input 12-lead ECG with the pre-stored coefficient set T for the specified 12-lead electrode placement. (b) Compute the three ST values for the VSLs: $ST_{LAD}$, $ST_{RCX}$, and $ST_{RCA}$ using either Equation (2) with ST results from Step 1.b or Equation (3) from the input 12-lead ST measurements with the pre-stored coefficient set T for the specified 12-lead electrode placement.

Step 3: If 12-lead ST measurements are not provided as part of the input, obtain the ST measurements for both the input 12-lead and the three VSLs using the existing ST measurement program in the host ECG device.

Step 4: Scale both the VSLs and the associated ST measurements using Equations (9)-(11) with pre-stored scale factors $S_{i,j}$, i=LAD, LCX, or RCA, and j=female, or male according to the input gender.

Step 5: Perform acute ischemia detection according to Equations (5) to (8) using pre-stored thresholds according to the input gender.

Figure 6:
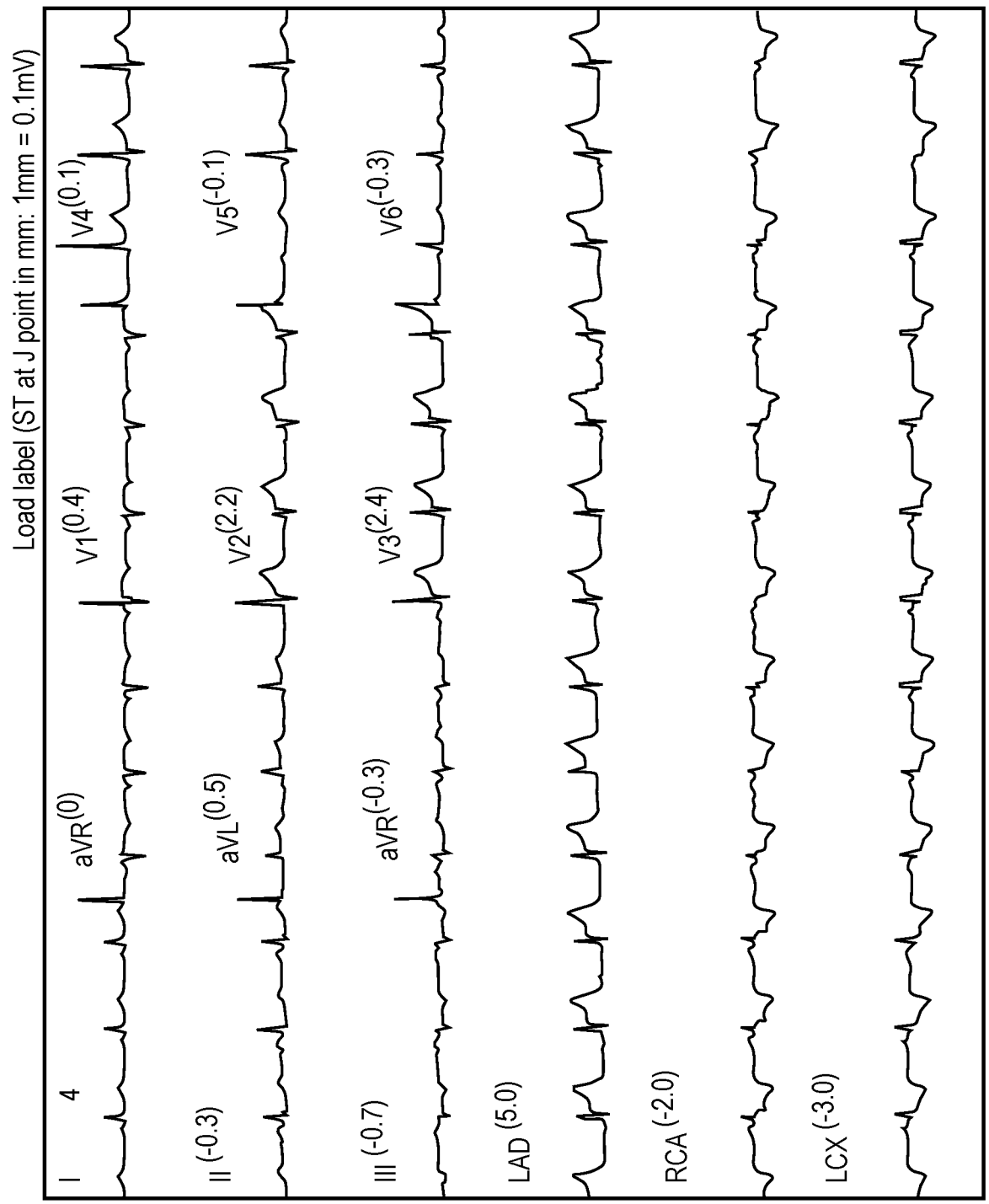
FIG. 6 illustrates one possible presentation of the vessel-specific lead (VSL) ECG derived using the system of FIGS. 1-3 together with the 12-lead ECG.

As an example, one possible presentation of the VSLs together with the 12-lead ECG is shown in FIG. 6. The 12-lead ECG in its standard 3×4 format is shown on top, and the three VSLs are shown in the bottom portion normally reserved for the rhythm strips. ST measurements are also displayed next to the lead labels for easy verification.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. An acute ischemia detection device comprising:
   a 12-lead electrocardiograph (ECG) device;
   an electronic data processing device programmed to perform operations including:
      applying the 12-lead ECG device to vessel-specific lead (VSL) transforms to 12-lead ECG data acquired by the 12-lead ECG device to generate VSL lead data,
      determining ST values for the VSL lead data, and
      deciding whether the 12-lead ECG data acquired by the 12-lead ECG device indicates acute ischemia by comparing each ST value for the VSL lead data with respective VSL lead ST thresholds; and
   a display component configured to display an acute ischemia alarm or warning after the decision is the 12-lead ECG data acquired by the 12-lead ECG device indicates the acute ischemia, wherein the deciding is not based on baseline 12 lead ECG data that is known not to indicate the acute ischemia.

2. The acute ischemia detection device of claim 1, wherein the applying includes:
   choosing the 12-lead ECG to VSL transforms for either a standard 12-lead ECG electrode placement or a Mason-Likar 12-lead ECG electrode placement based on the 12-lead ECG electrode placement used to acquire the 12-lead ECG data.

3. The acute ischemia detection device of claim 1, wherein the deciding includes:
   choosing the VSL lead ST thresholds based on a gender of a subject for which the 12-lead ECG data is acquired.

4. The acute ischemia detection device of claim 1, wherein the applying includes:
   applying a 12-lead ECG to left anterior descending (LAD) artery transform to 12-lead ECG data acquired by the 12-lead ECG device to generate LAD lead data;
   applying a 12-lead ECG to left circumflex (LCX) artery transform to 12-lead ECG data acquired by the 12-lead ECG device to generate LCX lead data; and
   applying a 12-lead ECG to left right coronary artery (RCA) transform to 12-lead ECG data acquired by the 12-lead ECG device to generate RCA lead data.

5. The acute ischemia detection device of claim 1, wherein the display component is further configured to display the generated VSL lead data as VSL lead traces.

6. The acute ischemia detection device of claim 1, further comprising:
   an electronic data processing device programmed to perform offline operations of:
      generating an ST map for each VSL based on at least one body surface potentials mapping (BSPM) dataset acquired with a coronary artery corresponding to the VSL occluded;
      identifying locations for each VSL at which the ST map shows a maximum ST elevation and a maximum ST depression; and
      determining the 12-lead ECG to VSL transform using the at least one BSPM dataset and the identified locations for each VSL.

7. The acute ischemia detection device of claim 6, wherein the electronic data processing device is programmed to perform further offline operations of:
   optimizing the VSL lead ST thresholds to optimally decide the acute ischemia for 12-lead ECG training data labeled as to whether the 12-lead ECG training data are for a subject with the acute ischemia or without the acute ischemia.

8. An acute ischemia detection method comprising:
   acquiring 12-lead electrocardiograph (ECG) data for a subject;
   applying the 12-lead ECG data to vessel-specific lead (VSL) transforms to the 12-lead ECG data to generate VSL lead data for the subject;
   determining ST values for the VSL lead data;
   deciding whether the subject has acute ischemia by comparing each ST value for the VSL lead data with respective VSL lead ST thresholds;
   issuing an acute ischemia alarm or warning after the decision is that the subject has the acute ischemia wherein the deciding is not based on baseline 12 lead ECG data that is known not to indicate the acute ischemia.

* * * * *